United States Patent

Cargnino et al.

[11] 4,104,139
[45] Aug. 1, 1978

[54] ELECTROPLATING ZINC

[75] Inventors: Francesco Cargnino, Venaria (Turin); Giorgio Audisio, Turin, Italy

[73] Assignee: Hoechst Aktiengesellschaft, Frankfurt, Fed. Rep. of Germany

[21] Appl. No.: 810,732

[22] Filed: Aug. 4, 1977

[51] Int. Cl.$^2$ .............................................. C25D 3/22
[52] U.S. Cl. ................................................. 204/55 R
[58] Field of Search ................. 204/55 R, 55 Y, 43 Z, 204/114

[56] References Cited

U.S. PATENT DOCUMENTS 4,049,510  9/1977  Rosenberg .......................... 204/55 R Primary Examiner—G. L. Kaplan
Attorney, Agent, or Firm—Connolly and Hutz

[57] ABSTRACT

Aqueous, alkaline, zinc-containing plating bath contains as complexing and equalizing agent a reaction product of phosphoric acid or polyphosphoric acid with a compound of the formula

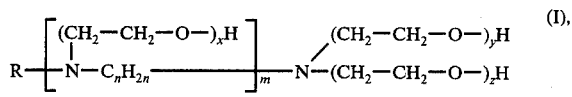

in which
R represents methyl, ethyl, hydroxyethyl or hydrogen,
$n$ is 2, 3 or 4, preferably 2 or 3,
$m$ is in the range of from 1 to 5, preferably 1 to 3,
$x$ and $y$ are 1 or 2, preferably 1 and
$z$ is 0 to 1, and optionally known brightening agents and/or wetting agents. It is used for the electrodeposition of zinc.

5 Claims, No Drawings

ELECTROPLATING ZINC

In industry cyanides are mainly used as complexing and equalizing agents in the electrodeposition of zinc from alkaline baths. A very satisfactory zinc coat is obtained from such an alkaline zinc cyanide bath optionally containing further additives, for example brightening or wetting agents. Because of their toxicity, the cyanide baths have, however, serious drawbacks as regards manipulation, effluent disposal and storage.

Therefore, attempts have been made to replace the cyanide in the electrodeposition from alkaline baths by other auxiliaries which do not have especially the disadvantage of high toxicity. Galvanization auxiliaries of this kind are, for example, hydroxylamines such as triethanolamine. With these products a satisfactory zinc coat can be obtained, but they have the disadvantage that in the usual after-treatment of the zinc coat in chromic acid baths a minor passivation of the zinc can be obtained only owing to the fact that the hydroxylamine forms complex compounds with iron which discharge at the cathode.

It has also been proposed to replace the cyanides in alkaline plating baths by polyammonium compounds, for example polyethylene imine quaternized with methyl chloride. But these polyammonium compounds cause the zinc coat to turn yellow in the passivation in the chromic acid bath. A further drawback resides in the fact that the complexing agents, proposed to replace the cyanides, should be used in relatively large amounts of from about 15 to 30 grams per liter.

It has now been found that phosphoric acid esters of polyalkylene amine oxalkylates as defined below do not have the disadvantages of the known complexing agents used in alkaline electrodeposition instead of cyanides.

The complexing agents to be used in accordance with the invention are alkali metal salts of reaction products of phosphoric acid or polyphosphoric acid with compounds of the formula

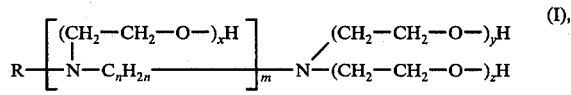

(I), in which

R represents methyl, ethyl, hydroxyethyl or hydrogen, n is 2,3, or 4, preferably 2 or 3, m is in the range of from 1 to 5, preferably 1 to 3, x and y are 1 or 2, preferably 1 and z is 0 or 1.

To prepare the complexing agents according to the invention the compounds of formula I are reacted for each OH equivalent with about 0.2 to 1.0 mol, preferably 0.3 to 0.8 mol of phosphoric acid or polyphosphoric acid, calculated as $P_2O_5$.

The present invention therefore provides aqueous alkaline zinc plating baths containing as complexing agent alkali metal salts of the reaction product of phosphoric acid or polyphosphoric acid with a compound of the aforesaid formula I and optionally the usual brightening agents and other galvanization auxiliaries.

The compounds of formula I can be prepared in known manner by reacting 2 to about 13 mols of ethylene oxide with 1 mol of an alkylene di- or polyamine, for example ethylene diamine, propylene diamine, N-methylpropylene diamine, N-methyldipropylene triamine, diethylene triamine, triethylene tetramine, or a mixture of such alkylene amides. In general, the compounds of formula I are obtained in the form of oils, which can be further reacted with phosphoric acid or polyphosphoric acid directly in this form without purification.

The reaction of alcohols with polyphosphoric acid is known for a long time (cf. Houben-Weyl, Methoden der organischen Chemie, volume XII/2, page 147). It yields predominantly phosphoric acid monoesters. To prepare the complexing agents to be used according to the invention it proved advantageous slowly to add, while stirring, the compound of formula I to the required amount of polyphosphoric acid at a rate such that the temperature is kept in the range of from about 200° to 280° C, preferably 200° to 250° C. Instead of polyphosphoric acid there can also be used for the reaction a mixture of phosphoric acid and phosphorus pentoxide, which is first dehydrated at a temperature above 200° C and then reacted with the compounds of formula I. When the reaction is terminated, the mixture is allowed to cool and preferably at a temperature of from about 100° to 130° C hot water is added. Using two to three times the amount of water, calculated on the reaction product, an aqueous solution of the reaction product is obtained. This solution can be used directly or after neutralization with alkali metal hydroxide as complexing agents in the zinc plating baths according to the invention. If desired, the sodium phosphate formed in the reaction and subsequent neutralization, which separates from the solution of the reaction product in crystal form on prolonged standing, can be separated.

To prepare the reaction product from phosphoric acid and the compound of formula I it is suitable slowly to add the alkylene polyamine oxethylate of formula I, while stirring, to the phosphoric acid. The water originating from phosphoric acid and the water formed in the esterification is then removed from the reaction mixture by distillation with temperature increase, first at atmospheric pressure and then at a reduced pressure. This distillation of the water takes several hours and in general it is carried out until the mixture has a final temperature of 140° to 170° C. The reaction product is then advantageously diluted with hot water and optionally neutralized with alkali metal hydroxide.

For a better manipulation of the reaction products of phosphoric acid or polyphosphoric acid with compounds of formula I as complexing agents in the electrodeposition of zinc they are suitably diluted with water to obtain a solution of about 30 to 60% strength by weight. To prepare the plating baths the complexing agents of the invention are used in an amount of from about 1 to 10 grams per liter, preferably 2 to 6 grams per liter of bath.

In addition the zinc plating baths according to the invention contain the usual amount of about 5 to 30 grams, preferably 8 to 12 grams, of zinc oxide and about 70 to 250 grams, preferably 90 to 120 grams of alkali metal hydroxide, preferably sodium hydroxide. The plating baths may further contain the usual brightening agents, stabilizers and optionally wetting agents and other auxiliaries.

The complexing agents according to the invention are excellently compatible with the brightening agents generally used in plating baths containing cyanide and zinc. The brightening agents are generally used in an amount of from about 0.01 to 2.0 grams, preferably 0.05 to 0.5 gram per liter. There are cited by way of example anisaldehyde, salicylaldehyde, vanillin benzaldehyde, piperonal, cyclohexanone or heliotropine. Occasionally, bisulfite complex compounds or Schiff's bases of the aldehydes are also used. Other known brightening agents are thiourea-formaldehyde resins and products as described in French Pat. No. 1,503,205. The brightening agents are frequently used together with colloids such as gelatin, glue, dextrin, sugar dyes and polyvinyl alcohol, which simultaneously act as depolarization agents.

The electrodeposition of zinc from the plating baths according to the invention is performed under the conditions usual for cyanide-containing zinc baths, i.e. at a bath temperature of from about 18° to 35° C, a voltage of about 2 to 10 volts and current densities of about 1 to 10 amperes/dm². The zinc can be deposited with and without movement of the bath. The preplate treatment of the articles to be covered with a layer of zinc, for example pickling and ungreasing, as well as the postplate treatment of the zinc coat by a short dipping in an oxidizing acid, preferably a chromic acid bath, can be performed in usual manner.

The zinc coatings deposited from the plating baths of the invention containing a reaction product of phosphoric acid or polyphosphoric acid with a compound of formula I are characterized by very favorable properties in the following passivation in a chromic acid bath. During this after-treatment no detrimental dark colorations or yellowing of the zinc coat are observed as occur with the use of other non-cyanide complexing agents. These advantageous properties of the complexing agents of the invention as well as the fact that they can be used in a very low concentration constitute a considerable progress in the electrodeposition from cyanide-free baths.

The following examples illustrate the invention.

EXAMPLE 1 a. Preparation of a phosphoric acid ester

100 Grams of a reaction product of 4 mols of ethylene oxide with 1 mol of ethylene diamine were added while stirring over a period of 30 minutes to 100 grams of polyphosphoric acid (84% of $P_2O_5$), at a rate such that the temperature of the reaction mixture did not exceed 230° C. Next, the reaction mixture was allowed to cool to 110° C and 280 grams of water of 90° to 95° C were added while stirring. An aqueous solution of the reaction product was obtained which was neutralized by adding 45 grams of pulverized sodium hydroxide. In this manner, a 40% solution of the reaction product was obtained.

b. Preparation of the plating bath

A bath was prepared containing per liter
10 grams of pure zinc oxide
100 grams of sodium hydroxide and
8 cc of the solution of the phosphoric acid ester prepared as described sub (a)

In a Hull cell an electrodeposition was performed for 10 minutes at 20° to 30° C and 2 amperes, corresponding to a current density of 2 to 10 amperes/dm². An opaque, firmly adhering non dusty deposit was obtained.

EXAMPLE 2 a. Preparation of a phosphoric acid ester

Under the conditions set forth in Example 1(a) 100 grams of pholyphosphoric acid (84% $P_2O_5$) were reacted with 100 grams of an addition compound of 3 mols of ethylene oxide on 1 mol of diethylene triamine, the reaction mixture was diluted and neutralized with sodium hydroxide.

b. In a Hull cell an electrodeposition was performed in a bath containing per liter
10 grams of pure zinc oxide
100 grams of sodium hydroxide and
8 cc of a 40% solution of the phosphoric acid ester obtained as set forth sub (a)

at 20° to 30° C and 2 amperes, corresponding to a current density of 2 to 10 amperes/dm².

After 10 minutes an opaque, uniform and firmly adhering, non dusty deposit was obtained, which had a brilliant appearance on the side of the lower current density and which could be passivated in a chromic acid bath without discoloration.

EXAMPLE 3 a. Preparation of a phosphoric acid ester

150 Grams of a reaction product of 3 mols ethylene oxide with 1 mol of diethylene triamine were added while stirring within 30 minutes to 490 grams of phosphoric acid of 75% strength at a rate such that the temperature of the reaction mixture did not exceed 100° C. The water contained in the reaction mixture and formed by the esterification reaction was distilled off by gradually increasing the temperature to 150° C, first for 7 hours at atmospheric pressure and then for 12 hours at reduced pressure. Next, the reaction product was allowed to cool to 100° C and diluted with water to a concentration of 40% by weight.

b. In a Hull cell an electrodeposition was performed in an aqueous bath containing per liter
10 grams of pure zinc oxide
100 grams of sodium hydroxide
0.05 gram of polyvinyl alcohol
0.08 gram of an anisaldehyde-bisulfite complex compound
10 cc of the solution of the phosphoric acid ester obtained as described above for 10 minutes at 20° to 30° C at 2 amperes, corresponding to a current density of 2 to 10 amperes/dm². On the whole surface of the electrolyte a brilliant, firmly adhering non dusty zinc coat was obtained which could be well passivated without discoloration by dipping into an chromic acid bath.

What is claimed is:

1. Zinc-containing aqueous electroplating bath containing alkali metal hydroxide and, as complexing agent, a reaction product of phosphoric acid or polyphosphoric acid with a compound of the formula

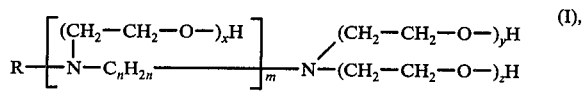

in which
R represents methyl, ethyl, hydroxyethyl or hydrogen,
$n$ is 2, 3 or 4,
$m$ is in the range of from 1 to 5,
$x$ and $y$ are 1 or 2, and
$z$ is 0 or 1.

2. Zinc plating bath as claimed in claim 1, wherein the complexing agent is a reaction product of 0.2 to 1.0 mol of phosphoric acid or polyphosphoric acid calculated as $P_2O_5$, for each hydroxyl equivalent of the compound of formula I.

3. Zinc plating bath as claimed in claim 1, containing 1 to 10 grams per liter of the reaction product of phosphoric acid or polyphosphoric acid with a compound of formula I.

4. Improvement in the process for electrodepositing zinc from an aqueous alkaline cyanide-free plating bath, which comprises using a bath containing, as complexing and equalizing agent, a reaction product of phosphoric acid or polyphosphoric acid with a compound of formula I as defined in claim 1 in an amount of from 1 to 10 grams per liter of bath.

5. Process for the electrodeposition of zinc as claimed in claim 4, wherein the bath used contains as complexing and equalized agent a reaction product of 0.2 to 1.0 mol of phosphoric acid or polyphosphoric acid, calculated as $P_2O_5$, for each hydroxyl equivalent of the compound of formula I as defined in claim 1.

* * * * *